US008192461B2

(12) United States Patent
Kochman et al.

(10) Patent No.: US 8,192,461 B2
(45) Date of Patent: Jun. 5, 2012

(54) METHODS FOR FACILITATING CLOSURE OF A BODILY OPENING USING ONE OR MORE TACKING DEVICES

(75) Inventors: Michael L. Kochman, Philadelphia, PA (US); Vihar C. Surti, Winston-Salem, NC (US)

(73) Assignees: Cook Medical Technologies LLC, Bloomington, IN (US); The Trustees of the University of Pennsylvania, Philadelphia, PA (US)

( * ) Notice: Subject to any disclaimer, the term of this patent is extended or adjusted under 35 U.S.C. 154(b) by 265 days.

(21) Appl. No.: 12/557,204

(22) Filed: Sep. 10, 2009

(65) Prior Publication Data

US 2010/0069955 A1    Mar. 18, 2010

Related U.S. Application Data

(60) Provisional application No. 61/096,197, filed on Sep. 11, 2008.

(51) Int. Cl.
*A61B 17/08* (2006.01)
(52) U.S. Cl. .......................... 606/216; 606/215; 606/151
(58) Field of Classification Search ................... 606/213, 606/215, 216, 232, 219, 220, 74, 75, 151, 606/142, 143, 103, 127, 139; 135/118
See application file for complete search history.

(56) References Cited

U.S. PATENT DOCUMENTS

| 363,538 A | * | 5/1887 | William | .................. 606/215 |
| 2,199,025 A | | 4/1940 | Conn | |
| 2,671,444 A | | 3/1954 | Pease, Jr. | |
| 3,209,422 A | | 10/1965 | Dritz | |
| 3,399,432 A | | 9/1968 | Merser | |
| 3,470,834 A | | 10/1969 | Bone | |
| 3,556,079 A | | 1/1971 | Omizo | |

(Continued)

FOREIGN PATENT DOCUMENTS

EP    0310582 A1    4/1989

(Continued)

OTHER PUBLICATIONS

Communication Pursuant to Rules 161(1) and 162EPC for European Patent Application Serial No. 09791618.3, dated Mar. 28, 2011, 2 pages.

(Continued)

*Primary Examiner* — Julian Woo
*Assistant Examiner* — Christopher L Templeton
(74) *Attorney, Agent, or Firm* — Brinks Hofer Gilson & Lione

(57) ABSTRACT

The present embodiments provide methods for facilitating closure of a bodily opening. In one exemplary method, at least a portion of a first tacking device is disposed through at least a portion of tissue at a first location in a vicinity of an opening in the tissue. Then, at least a portion of a second tacking device is disposed through at least a portion of tissue at a second location in the vicinity of an opening in the tissue. A closure member having at least one loop portion is advanced towards the first and second tacking devices, and the loop portion is positioned around at least a portion of the first tacking device and at least a portion of the second tacking device. The closure member then is actuated to urge the first tacking device towards the second tacking device to provide a compressive force upon the opening.

22 Claims, 7 Drawing Sheets

U.S. PATENT DOCUMENTS

| | | | |
|---|---|---|---|
| 3,814,104 A | 6/1974 | Irnich et al. | |
| 3,856,016 A | 12/1974 | Davis | |
| 3,954,108 A | 5/1976 | Davis | |
| 3,958,576 A | 5/1976 | Komiya | |
| 4,006,747 A | 2/1977 | Kronenthal et al. | |
| 4,204,541 A | 5/1980 | Kapitanov | |
| 4,217,902 A | 8/1980 | March | |
| 4,235,238 A | 11/1980 | Ogiu et al. | |
| 4,485,816 A | 12/1984 | Krumme | |
| 4,621,639 A | 11/1986 | Transue et al. | |
| 4,749,114 A | 6/1988 | Green | |
| 4,773,420 A | 9/1988 | Green | |
| 4,791,707 A | 12/1988 | Tucker | |
| 4,796,627 A | 1/1989 | Tucker | |
| 4,821,939 A | 4/1989 | Green | |
| 4,832,027 A | 5/1989 | Utz | |
| 4,990,156 A | 2/1991 | Lefebvre | |
| 5,015,249 A | 5/1991 | Nakao et al. | |
| 5,049,153 A | 9/1991 | Nakao et al. | |
| 5,059,205 A | 10/1991 | El-Nounou et al. | |
| 5,084,057 A | 1/1992 | Green et al. | |
| 5,099,827 A | 3/1992 | Melzer et al. | |
| 5,100,420 A | 3/1992 | Green et al. | |
| 5,123,914 A | 6/1992 | Cope | |
| 5,156,609 A | 10/1992 | Nakao et al. | |
| 5,192,303 A | 3/1993 | Gatturna et al. | |
| 5,203,787 A | 4/1993 | Noblitt et al. | |
| 5,236,438 A * | 8/1993 | Wilk | 606/215 |
| 5,242,456 A | 9/1993 | Nash et al. | |
| 5,324,307 A | 6/1994 | Jarrett et al. | |
| 5,333,624 A | 8/1994 | Tovey | |
| 5,334,217 A | 8/1994 | Das | |
| 5,350,385 A | 9/1994 | Christy | |
| 5,366,480 A | 11/1994 | Corriveau et al. | |
| 5,368,600 A | 11/1994 | Failla et al. | |
| 5,368,602 A | 11/1994 | de la Torre | |
| 5,411,522 A | 5/1995 | Trott | |
| 5,417,691 A | 5/1995 | Hayhurst | |
| 5,437,266 A | 8/1995 | McPherson | |
| 5,520,700 A | 5/1996 | Beyar et al. | |
| 5,527,343 A | 6/1996 | Bonutti | |
| 5,554,183 A | 9/1996 | Nazari | |
| 5,573,543 A | 11/1996 | Akopov et al. | |
| 5,582,615 A | 12/1996 | Foshee et al. | |
| 5,582,616 A | 12/1996 | Bolduc et al. | |
| 5,593,414 A | 1/1997 | Shipp et al. | |
| 5,662,683 A | 9/1997 | Kay | |
| 5,667,527 A | 9/1997 | Cook et al. | |
| 5,674,231 A | 10/1997 | Green et al. | |
| 5,690,656 A | 11/1997 | Cope et al. | |
| 5,695,525 A | 12/1997 | Mulhauser et al. | |
| 5,702,421 A * | 12/1997 | Schneidt | 606/213 |
| 5,728,116 A | 3/1998 | Rosenman | |
| 5,741,278 A | 4/1998 | Stevens | |
| 5,779,720 A | 7/1998 | Walder-Utz et al. | |
| 5,810,848 A | 9/1998 | Hayhurst | |
| 5,865,791 A | 2/1999 | Whayne et al. | |
| 5,868,763 A | 2/1999 | Spence et al. | |
| 5,891,159 A | 4/1999 | Sherman et al. | |
| 5,893,856 A * | 4/1999 | Jacob et al. | 606/151 |
| 5,968,078 A | 10/1999 | Grotz | |
| 5,972,002 A | 10/1999 | Bark et al. | |
| 5,972,022 A | 10/1999 | Huxel | |
| 5,976,159 A | 11/1999 | Bolduc et al. | |
| 5,984,917 A | 11/1999 | Fleischman et al. | |
| 5,984,949 A | 11/1999 | Levin | |
| 6,110,183 A | 8/2000 | Cope | |
| 6,113,612 A | 9/2000 | Swanson et al. | |
| RE36,974 E | 11/2000 | Bonutti | |
| 6,149,658 A | 11/2000 | Gardiner et al. | |
| 6,152,935 A | 11/2000 | Kammerer et al. | |
| 6,152,937 A | 11/2000 | Peterson et al. | |
| 6,156,044 A | 12/2000 | Kammerer et al. | |
| 6,159,223 A | 12/2000 | Danks et al. | |
| 6,171,321 B1 | 1/2001 | Gifford, III et al. | |
| 6,183,486 B1 | 2/2001 | Snow et al. | |
| 6,193,732 B1 | 2/2001 | Frantzen et al. | |
| 6,228,055 B1 | 5/2001 | Foerster et al. | |
| 6,241,747 B1 | 6/2001 | Ruff | |
| 6,290,674 B1 | 9/2001 | Roue et al. | |
| 6,306,150 B1 | 10/2001 | Levinson | |
| 6,328,727 B1 | 12/2001 | Frazier et al. | |
| 6,352,503 B1 * | 3/2002 | Matsui et al. | 600/104 |
| 6,371,963 B1 | 4/2002 | Nishtala et al. | |
| 6,402,765 B1 | 6/2002 | Monassevitch et al. | |
| 6,419,669 B1 | 7/2002 | Frazier et al. | |
| 6,425,887 B1 | 7/2002 | McGuckin et al. | |
| 6,425,900 B1 | 7/2002 | Knodel et al. | |
| 6,428,548 B1 | 8/2002 | Durgin et al. | |
| 6,446,854 B1 | 9/2002 | Remiszewski et al. | |
| 6,447,530 B1 | 9/2002 | Ostrovsky et al. | |
| 6,468,290 B1 | 10/2002 | Weldon et al. | |
| 6,482,178 B1 | 11/2002 | Andrews et al. | |
| 6,491,707 B2 | 12/2002 | Makower et al. | |
| 6,551,333 B2 | 4/2003 | Kuhns et al. | |
| 6,572,629 B2 | 6/2003 | Kalloo et al. | |
| 6,592,559 B1 | 7/2003 | Pakter et al. | |
| 6,623,510 B2 | 9/2003 | Carley et al. | |
| 6,641,557 B1 | 11/2003 | Frazier et al. | |
| 6,699,256 B1 | 3/2004 | Logan et al. | |
| 6,699,263 B2 | 3/2004 | Cope | |
| 6,712,804 B2 | 3/2004 | Roue et al. | |
| 6,719,777 B2 | 4/2004 | Ginn et al. | |
| 6,746,458 B1 | 6/2004 | Cloud | |
| 6,746,460 B2 | 6/2004 | Gannoe et al. | |
| 6,746,472 B2 | 6/2004 | Frazier et al. | |
| 6,776,783 B1 | 8/2004 | Frantzen et al. | |
| 6,849,078 B2 | 2/2005 | Durgin et al. | |
| 6,884,248 B2 | 4/2005 | Bolduc et al. | |
| 6,911,032 B2 | 6/2005 | Jugenheimer et al. | |
| 6,913,607 B2 | 7/2005 | Ainsworth et al. | |
| 6,966,916 B2 | 11/2005 | Kumar | |
| 6,994,713 B2 | 2/2006 | Berg et al. | |
| 7,001,398 B2 | 2/2006 | Carley et al. | |
| 7,018,388 B2 | 3/2006 | Yencho et al. | |
| 7,025,756 B2 | 4/2006 | Frazier et al. | |
| 7,056,325 B1 | 6/2006 | Makower et al. | |
| 7,060,084 B1 | 6/2006 | Loshakove et al. | |
| 7,087,073 B2 | 8/2006 | Bonutti | |
| 7,112,214 B2 | 9/2006 | Peterson et al. | |
| 7,115,110 B2 | 10/2006 | Frazier et al. | |
| 7,211,101 B2 | 5/2007 | Carley et al. | |
| 7,326,221 B2 | 2/2008 | Sakamoto | |
| 7,326,231 B2 | 2/2008 | Phillips et al. | |
| 7,331,968 B2 | 2/2008 | Arp et al. | |
| 7,410,460 B2 | 8/2008 | Benderev | |
| 7,416,554 B2 | 8/2008 | Lam et al. | |
| 7,485,124 B2 | 2/2009 | Kuhns et al. | |
| 7,494,496 B2 | 2/2009 | Swain et al. | |
| 7,575,586 B2 * | 8/2009 | Berg et al. | 606/215 |
| 7,601,159 B2 | 10/2009 | Ewers et al. | |
| 7,608,091 B2 | 10/2009 | Goldbarb et al. | |
| 7,618,426 B2 | 11/2009 | Ewers et al. | |
| 7,621,925 B2 | 11/2009 | Saadat et al. | |
| 7,622,068 B2 | 11/2009 | Li et al. | |
| 7,641,836 B2 | 1/2010 | Li et al. | |
| 7,655,015 B2 | 2/2010 | Goldfarb et al. | |
| 7,666,197 B2 | 2/2010 | Orban, III | |
| 7,670,362 B2 | 3/2010 | Zergiebel | |
| 7,695,493 B2 | 4/2010 | Saadat et al. | |
| 7,704,264 B2 | 4/2010 | Ewers et al. | |
| 7,722,628 B2 | 5/2010 | Stokes et al. | |
| 7,727,247 B2 | 6/2010 | Kimura et al. | |
| 7,727,248 B2 | 6/2010 | Smith et al. | |
| 7,736,376 B2 | 6/2010 | Sato et al. | |
| 7,736,378 B2 | 6/2010 | Maahs et al. | |
| 7,736,379 B2 | 6/2010 | Ewers et al. | |
| 7,736,388 B2 | 6/2010 | Goldfarb et al. | |
| 7,744,613 B2 | 6/2010 | Ewers et al. | |
| 7,758,598 B2 | 7/2010 | Conlon et al. | |
| 7,758,612 B2 | 7/2010 | Shipp | |
| 7,799,040 B2 | 9/2010 | Stokes et al. | |
| 7,803,165 B2 | 9/2010 | Stokes et al. | |
| 7,803,166 B2 | 9/2010 | Stokes et al. | |
| 7,815,652 B2 | 10/2010 | Messerly et al. | |
| 7,815,653 B2 | 10/2010 | Stokes et al. | |
| 7,815,659 B2 | 10/2010 | Conlon et al. | |

| | | | |
|---|---|---|---|
| 7,815,662 B2 | 10/2010 | Spivey et al. | |
| 7,828,811 B2 | 11/2010 | Kortenbach et al. | |
| 7,914,542 B2 * | 3/2011 | Lamson et al. | 606/139 |
| 7,972,362 B2 * | 7/2011 | Wilke et al. | 606/216 |
| 2001/0002250 A1 | 5/2001 | Burbank et al. | |
| 2001/0037130 A1 | 11/2001 | Adams | |
| 2001/0039435 A1 | 11/2001 | Roue et al. | |
| 2003/0158578 A1 | 8/2003 | Pantages et al. | |
| 2003/0163160 A1 * | 8/2003 | O'Malley et al. | 606/213 |
| 2003/0195561 A1 | 10/2003 | Carley et al. | |
| 2004/0009289 A1 | 1/2004 | Carley et al. | |
| 2004/0039414 A1 | 2/2004 | Carley et al. | |
| 2004/0044364 A1 | 3/2004 | Devries et al. | |
| 2004/0073236 A1 | 4/2004 | Carley et al. | |
| 2004/0087981 A1 | 5/2004 | Berube et al. | |
| 2004/0087985 A1 | 5/2004 | Loshakove et al. | |
| 2004/0092975 A1 | 5/2004 | Loshakove et al. | |
| 2004/0097982 A1 | 5/2004 | Jugenheimer et al. | |
| 2004/0167539 A1 | 8/2004 | Kuehn et al. | |
| 2004/0186514 A1 | 9/2004 | Swain et al. | |
| 2004/0220596 A1 | 11/2004 | Frazier et al. | |
| 2005/0015141 A1 | 1/2005 | Quiachon et al. | |
| 2005/0033313 A1 | 2/2005 | Chu et al. | |
| 2005/0038370 A1 | 2/2005 | Kuth et al. | |
| 2005/0075654 A1 * | 4/2005 | Kelleher | 606/151 |
| 2005/0113851 A1 | 5/2005 | Swain et al. | |
| 2005/0119695 A1 | 6/2005 | Carley et al. | |
| 2005/0143763 A1 | 6/2005 | Ortiz et al. | |
| 2005/0171562 A1 | 8/2005 | Criscuolo et al. | |
| 2005/0182445 A1 | 8/2005 | Zamierowski | |
| 2005/0192596 A1 | 9/2005 | Jugenheimer et al. | |
| 2005/0197594 A1 | 9/2005 | Burbank et al. | |
| 2005/0234512 A1 | 10/2005 | Nakao | |
| 2005/0251165 A1 | 11/2005 | Vaughan et al. | |
| 2005/0267524 A1 * | 12/2005 | Chanduszko | 606/213 |
| 2005/0277945 A1 | 12/2005 | Saadat et al. | |
| 2005/0277981 A1 | 12/2005 | Maahs et al. | |
| 2005/0283188 A1 | 12/2005 | Loshakove et al. | |
| 2006/0004409 A1 | 1/2006 | Nobis et al. | |
| 2006/0004410 A1 | 1/2006 | Nobis et al. | |
| 2006/0015006 A1 | 1/2006 | Laurence et al. | |
| 2006/0015125 A1 | 1/2006 | Swain | |
| 2006/0025788 A1 | 2/2006 | Loshakove et al. | |
| 2006/0025819 A1 | 2/2006 | Nobis et al. | |
| 2006/0106279 A1 | 5/2006 | Machold et al. | |
| 2006/0106405 A1 | 5/2006 | Fann et al. | |
| 2006/0116605 A1 | 6/2006 | Nakao | |
| 2006/0135989 A1 | 6/2006 | Carley et al. | |
| 2006/0155288 A1 | 7/2006 | Little et al. | |
| 2006/0167484 A1 | 7/2006 | Carley et al. | |
| 2006/0190016 A1 | 8/2006 | Onuki et al. | |
| 2006/0190038 A1 | 8/2006 | Carley et al. | |
| 2006/0206063 A1 | 9/2006 | Kagan et al. | |
| 2006/0207606 A1 | 9/2006 | Roue et al. | |
| 2006/0217762 A1 | 9/2006 | Maahs et al. | |
| 2006/0235447 A1 | 10/2006 | Walshe | |
| 2006/0237022 A1 | 10/2006 | Chen et al. | |
| 2006/0237023 A1 | 10/2006 | Cox et al. | |
| 2006/0241662 A1 | 10/2006 | Adams et al. | |
| 2006/0241691 A1 | 10/2006 | Wilk | |
| 2006/0253144 A1 | 11/2006 | Mikkaichi | |
| 2006/0271073 A1 | 11/2006 | Lam et al. | |
| 2006/0271101 A1 | 11/2006 | Saadat et al. | |
| 2007/0010835 A1 | 1/2007 | Breton et al. | |
| 2007/0100375 A1 | 5/2007 | Mikkaichi et al. | |
| 2007/0100376 A1 | 5/2007 | Mikkaichi et al. | |
| 2007/0112362 A1 | 5/2007 | Mikkaichi et al. | |
| 2007/0123840 A1 | 5/2007 | Cox | |
| 2007/0129755 A1 | 6/2007 | Abbott et al. | |
| 2007/0129756 A1 * | 6/2007 | Abbott et al. | 606/213 |
| 2007/0173868 A1 | 7/2007 | Bachinski et al. | |
| 2007/0208360 A1 | 9/2007 | Demarais et al. | |
| 2007/0219411 A1 | 9/2007 | Dejima et al. | |
| 2007/0270752 A1 | 11/2007 | LaBombard | |
| 2007/0270943 A1 | 11/2007 | Solem et al. | |
| 2007/0276416 A1 | 11/2007 | Ginn et al. | |
| 2007/0276424 A1 | 11/2007 | Mikkaichi et al. | |
| 2008/0015633 A1 | 1/2008 | Abbott et al. | |
| 2008/0086153 A1 | 4/2008 | Sakamoto et al. | |
| 2008/0091059 A1 | 4/2008 | Machold |
| 2008/0097489 A1 | 4/2008 | Goldfarb et al. |
| 2008/0114378 A1 | 5/2008 | Matsushita |
| 2008/0114398 A1 | 5/2008 | Phillips et al. |
| 2008/0147116 A1 | 6/2008 | Smith et al. |
| 2008/0154290 A1 | 6/2008 | Golden et al. |
| 2008/0172088 A1 | 7/2008 | Smith et al. |
| 2008/0177304 A1 | 7/2008 | Westra et al. |
| 2008/0200930 A1 | 8/2008 | Saadat et al. |
| 2008/0208161 A1 | 8/2008 | Kaji et al. |
| 2008/0208214 A1 | 8/2008 | Sato et al. |
| 2008/0208218 A1 | 8/2008 | Shiono |
| 2008/0208219 A1 | 8/2008 | Suzuki |
| 2008/0208220 A1 | 8/2008 | Shiono et al. |
| 2008/0208251 A1 | 8/2008 | Weadock et al. |
| 2008/0221619 A1 | 9/2008 | Spivey et al. |
| 2008/0228199 A1 | 9/2008 | Cropper et al. |
| 2008/0228202 A1 | 9/2008 | Cropper et al. |
| 2008/0228203 A1 | 9/2008 | Bell et al. |
| 2008/0243148 A1 | 10/2008 | Mikkaichi et al. |
| 2008/0255422 A1 | 10/2008 | Kondoh et al. |
| 2008/0255423 A1 | 10/2008 | Kondo et al. |
| 2008/0262525 A1 | 10/2008 | Chang et al. |
| 2008/0269566 A1 | 10/2008 | Measamer |
| 2008/0275297 A1 | 11/2008 | Bakos et al. |
| 2008/0281354 A1 | 11/2008 | Cropper et al. |
| 2008/0294178 A1 | 11/2008 | Kortenbach et al. |
| 2008/0296344 A1 | 12/2008 | Cropper et al. |
| 2008/0300547 A1 | 12/2008 | Bakos |
| 2008/0300608 A1 | 12/2008 | Measamer |
| 2008/0300624 A1 | 12/2008 | Schwemberger et al. |
| 2008/0300627 A1 | 12/2008 | Measamer et al. |
| 2008/0319257 A1 | 12/2008 | Sato et al. |
| 2009/0005800 A1 | 1/2009 | Franer et al. |
| 2009/0018552 A1 | 1/2009 | Lam et al. |
| 2009/0069822 A1 | 3/2009 | Takahashi et al. |
| 2009/0088780 A1 | 4/2009 | Shiono et al. |
| 2009/0088797 A1 | 4/2009 | Crombie et al. |
| 2009/0125038 A1 | 5/2009 | Ewers et al. |
| 2009/0125039 A1 | 5/2009 | Mikkaichi et al. |
| 2009/0204147 A1 | 8/2009 | Rahmani |
| 2009/0222029 A1 | 9/2009 | Gordin et al. |
| 2009/0287080 A1 | 11/2009 | Nishina et al. |
| 2009/0299385 A1 | 12/2009 | Stefanchik et al. |
| 2009/0299406 A1 | 12/2009 | Swain et al. |
| 2009/0306686 A1 | 12/2009 | Ohdaira |
| 2009/0318936 A1 | 12/2009 | Harris et al. |
| 2009/0326578 A1 | 12/2009 | Ewers et al. |
| 2010/0010457 A1 | 1/2010 | Ewers et al. |
| 2010/0010508 A1 | 1/2010 | Takahashi et al. |
| 2010/0010509 A1 | 1/2010 | Ishioka et al. |
| 2010/0010511 A1 | 1/2010 | Harris et al. |
| 2010/0010514 A1 | 1/2010 | Ishioka et al. |
| 2010/0010520 A1 | 1/2010 | Takahashi et al. |
| 2010/0042115 A1 | 2/2010 | Saadat et al. |
| 2010/0042144 A1 | 2/2010 | Bennett |
| 2010/0049244 A1 | 2/2010 | Cohen et al. |
| 2010/0076462 A1 | 3/2010 | Bakos et al. |
| 2010/0076488 A1 | 3/2010 | Spivey et al. |
| 2010/0094341 A1 | 4/2010 | Raju |
| 2010/0106166 A1 | 4/2010 | Cropper et al. |
| 2010/0113873 A1 | 5/2010 | Suzuki et al. |
| 2010/0121351 A1 | 5/2010 | Whitfield et al. |
| 2010/0174312 A1 | 7/2010 | Maahs et al. |
| 2010/0198192 A1 | 8/2010 | Serina et al. |
| 2010/0211086 A1 | 8/2010 | Ewers et al. |
| 2010/0217292 A1 | 8/2010 | Kimura et al. |
| 2010/0217293 A1 | 8/2010 | Kimura et al. |
| 2010/0217294 A1 | 8/2010 | Kimura et al. |
| 2010/0249498 A1 | 9/2010 | Wingardner et al. |
| 2010/0256658 A1 | 10/2010 | Criscuolo et al. |
| 2010/0264192 A1 | 10/2010 | Marczyk |
| 2010/0268253 A1 | 10/2010 | Ahlberg et al. |
| 2010/0268270 A1 | 10/2010 | Viola |
| 2011/0022065 A1 | 1/2011 | Shipp |

FOREIGN PATENT DOCUMENTS

| | | |
|---|---|---|
| EP | 0774237 A2 | 5/1997 |
| EP | 1317904 A1 | 11/2003 |

| | | |
|---|---|---|
| EP | 1961388 A2 | 8/2008 |
| WO | WO88/01486 | 3/1988 |
| WO | WO90/02522 | 3/1990 |
| WO | WO95/21575 | 8/1995 |
| WO | WO96/14020 | 5/1996 |
| WO | WO96/40356 | 12/1996 |
| WO | WO98/18389 | 5/1998 |
| WO | WO99/62408 | 12/1999 |
| WO | WO00/07506 | 2/2000 |
| WO | WO00/16701 | 3/2000 |
| WO | WO00/21443 | 4/2000 |
| WO | WO00/56223 | 9/2000 |
| WO | WO00/56227 | 9/2000 |
| WO | WO01/19256 | 3/2001 |
| WO | WO01/35832 | 5/2001 |
| WO | WO01/58363 | 8/2001 |
| WO | WO2005/034729 | 4/2005 |
| WO | WO2007/004228 | 1/2007 |
| WO | WO2007/024615 | 3/2007 |
| WO | WO2007/089843 | 8/2007 |
| WO | WO2007/142977 | 12/2007 |

OTHER PUBLICATIONS

Response to Communication Pursuant to Rules 161(1) and 162EPC for European Patent Application Serial No. 09791618.3, dated May 6, 2011, 4 pages.
International Search Report for PCT/US2009/041415, dated Jul. 24, 2009, 4 pages.
International Preliminary Report on Patentability for PCT/US2009/041415, dated Nov. 4, 2010, 6 pages.
International Search Report for PCT/US2009/054176, dated Nov. 20, 2009, 16 pages.
International Preliminary Report on Patentability for PCT/US2009/054176, dated Mar. 3, 2011, 9 pages.
International Search Report for PCT/US2009/056512, dated Feb. 10, 2010, 5 pages.
Article 34 Demand and Amendment for PCT/US2009/056512, dated Jul. 6, 2010, 22 pages.
International Preliminary Report on Patentability for PCT/US2009/056512, dated Jan. 10, 2010, 31 pages.
International Search Report and Written Opinion for PCT/US2009/056604, dated May 4, 2010, 9 pages.
International Search Report for PCT/US2009/066983, dated Jan. 19, 2010, 4 pages.
International Search Report and Written Opinion for PCT/US2009/066992, dated Mar. 4, 2010, 15 pages.
International Search Report and Written Opinion for PCT/US2009/067992, Jul. 9, 2010, 20 pages.
International Search Report and Written Opinion for PCT/US2009/067994, dated Jun. 10, 2010, 18 pages.
International Search Report and Written Opinion for PCT/US2010/036188, dated Sep. 14, 2010, 18 pages.
Restriction Requirement for U.S. Appl. No. 12/428,226, dated Apr. 27, 2011, 7 pages.
Response to Restriction Requirement for U.S. Appl. No. 12/428,226, dated May 27, 2011, 10 pages.
Office Action for U.S. Appl. No. 12/428,226, dated Jun. 9, 2011, 8 pages.
Office Action for U.S. Appl. No. 12/543,000, dated Mar. 15, 2011, 14 pages.
Fritscher-Ravens, "Transgastric endoscopy- a new fashion, a new excitement!", *Endoscopy*, vol. 39, 2007, pp. 161-167.
Sporn et al., "Endoscopic colotomy closure after full thickness excision: comparison of T fastener with mutliclip applier", *Endoscopy*, vol. 40, 2008, pp. 589-594.
Voermans et al., "In vitro comparison and evaluation of seven gastric closure modalities for natural orifice transluminal endoscopic surgery", Endoscopy, vol.. 40, 2008, pp. 595-601.
Sclabas et al., "Endoluminal Methods for Gastrotomy Closure in Natural Orifice TransEnteric Surgery", *Surgical Innovation*, vol., 13, No. 1, Mar. 2006, pp. 23-30.
Desilets et al., "Loop-anchor purse-string versus endoscopic clips for gastric closure: a natural orifice transluminal endoscopic surgery comparison study using burst pressures", *Gastrointestinal Endoscopy*, vol. 70, No. 6, 2009, pp. 1225-1230.
Sporn et al., "Endoscopic colotomy closure for natural orifice transluminal endoscopic surgery using a T-fastener protoype in comparison to conventional laparoscopic suture closure", *Gastrointestinal Endoscopy*, vol. 68, No. 4, 2008, pp. 724-730.
Dray et al., "Air and fluid leak tests after NOTES procedures: a pilot study in a live porcine model ", *Gastrointestinal Endoscopy*, vol. 68, No. 3, 2008, pp. 513-519.
Shurr et al., "An over-the-scope clip (OTSC) system for closure of iatrogenic colon perforations: results of an experimental survival study in pigs", *Endoscopy*, vol. 40, 2008, pp. 584-588.
Romanelli et al, "Natural orifice transluminal endoscopic surgery gastrotomy closure in porcine explants with the Padlock-G clip using the Lock-It system", *Endoscopy*, vol. 42, 2010, pp. 306-310.
Bergström et al., "Early clinical experience with a new flexible endoscopic suturing method for natural orifice transluminal endoscopic surgery and intraluminal endosurgery", *Gastrointestinal Endoscopy*, vol. 67, No. 3, 2008, pp. 528-533.
Park et al, "Endoscopic sutured closure of a gastric natural orifice transluminal endoscopic surgery access gastronomy compared with open surgical closure in a porcine model. A randomized, multicenter controlled trial", *Endoscopy*, vol. 42, 2010 pp. 311-317.
Yasser M. Bhat, MD, "Transluminal Endosurgery: Novel Use of Endoscopic Tacks for the Closure of Access Sites in Natural Orifice Transluminal Endoscopic Surgery," *Gastrointestinal Endoscopy*, vol. 69, No. 6, p. 1161.

* cited by examiner

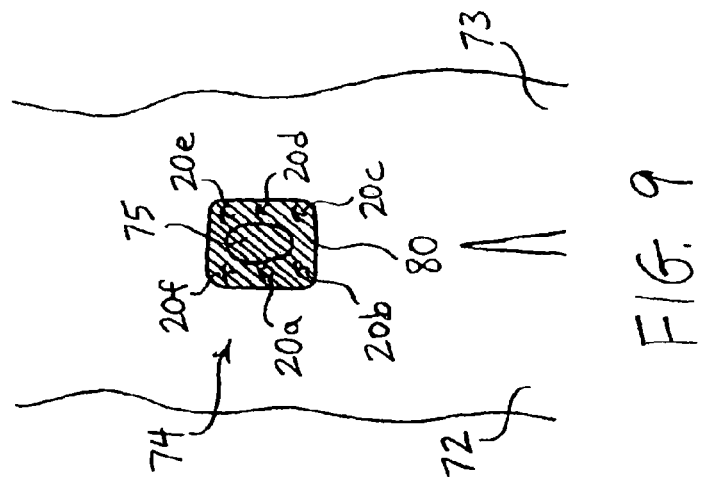
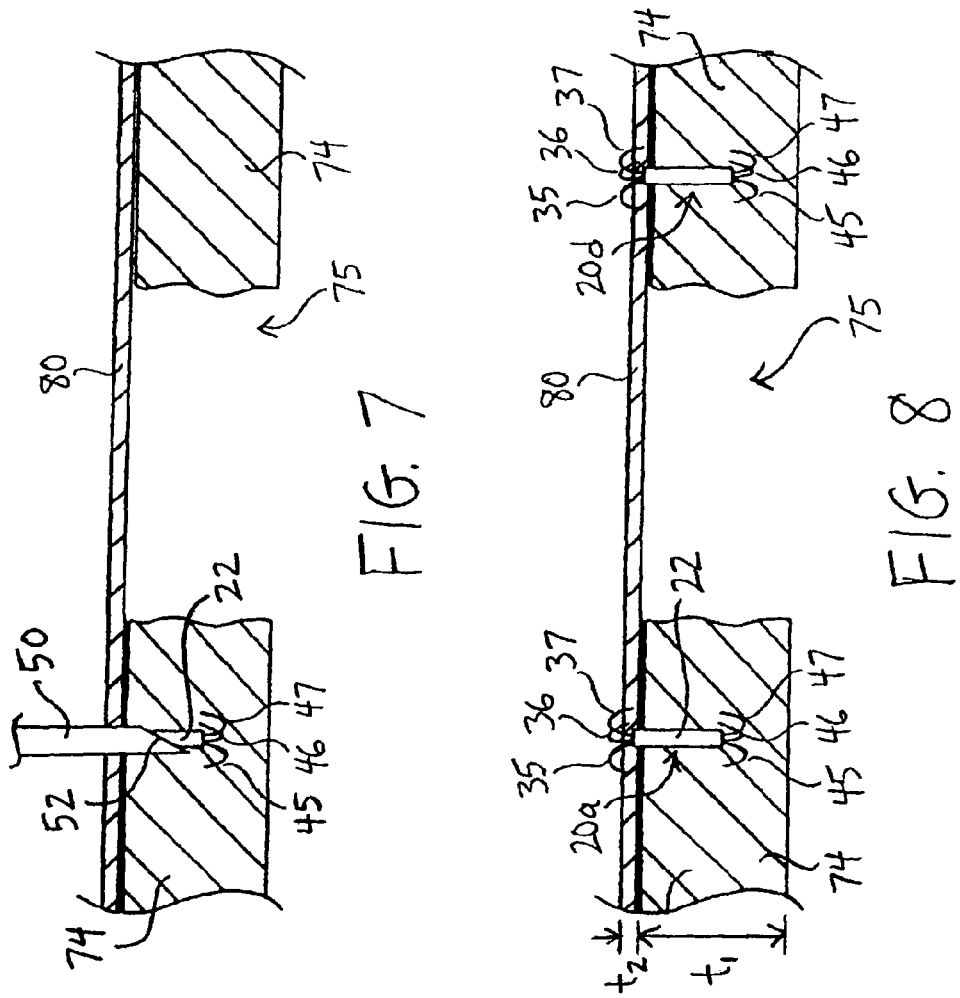

METHODS FOR FACILITATING CLOSURE OF A BODILY OPENING USING ONE OR MORE TACKING DEVICES

PRIORITY CLAIM

This invention claims the benefit of priority of U.S. Provisional Application Ser. No. 61/096,197, entitled "Methods for Facilitating Closure of a Bodily Opening Using One or More Tacking Devices," filed Sep. 11, 2008, the disclosure of which is hereby incorporated by reference in its entirety.

BACKGROUND

The present embodiments relate generally to medical devices, and more particularly, to methods for facilitating closure of a bodily opening.

Perforations in tissue or bodily walls may be formed intentionally or unintentionally. For example, an unintentional ventral abdominal hernia may be formed in the abdominal wall due to heavy lifting, coughing, strain imposed during a bowel movement or urination, fluid in the abdominal cavity, or other reasons.

Intentional perforations may be formed, for example, during surgical procedures such as translumenal procedures. In a translumenal procedure, one or more instruments, such as an endoscope, may be inserted through a visceral wall, such as the stomach wall. During a translumenal procedure, a closure instrument may be used to close the perforation in the visceral wall. Depending on the structure comprising the perforation, it may be difficult to adequately close the perforation and prevent leakage of bodily fluids.

Attempts to seal perforations have been attempted by coupling a graft member to tissue. For example, during hernia repair, a graft material such as a mesh or patch may be disposed to cover the perforation. The graft material may completely overlap with the perforation, and the edges of the graft material may at least partially overlap with tissue surrounding the perforation. The graft material then may be secured to the surrounding tissue in an attempt to effectively cover and seal the perforation.

In order to secure the graft material to the surrounding tissue, sutures commonly are manually threaded through the full thickness of the surrounding tissue. In the case of a ventral abdominal hernia, the sutures may be threaded through the thickness of the abdominal wall, then tied down and knotted. However, such manual suturing techniques may be time consuming and/or difficult to perform.

Similarly, when closing intentional openings formed during translumenal procedures, suturing techniques may be used. However, the suturing techniques employed to close translumenal openings may be difficult to perform, may permit leakage of bodily fluids, and may be unreliable and difficult to reproduce.

SUMMARY

The present embodiments provide methods for facilitating closure of a bodily opening. In one exemplary method, at least a portion of a first tacking device is disposed through at least a portion of tissue at a first location in a vicinity of an opening in the tissue. Then, at least a portion of a second tacking device is disposed through at least a portion of the tissue at a second location in the vicinity of the opening in the tissue. A closure member having at least one loop portion is advanced towards the first and second tacking devices, and the loop portion is positioned around at least a portion of the first tacking device and at least a portion of the second tacking device. The closure member then is actuated to urge the first tacking device towards the second tacking device to apply a compressive force upon the opening.

In one embodiment, the first and second tacking devices each comprises at least one proximal deployable member having contracted and expanded states, and further each comprise at least one distal deployable member having contracted and expanded states. The proximal deployable member and the distal deployable member each may comprise hook-shaped configurations in the expanded states. The proximal and distal deployable members each may comprise a nickel-titanium alloy that is configured to self-expand to the hook-shaped configuration. In an exemplary embodiment, three distal deployable members are provided for engaging a serosal layer of tissue, while three proximal deployable members are provided for engaging a mucosal layer of the tissue.

The first and second tacking devices may be delivered to a target site using an insertion tool comprising a hollow lumen having an inner diameter configured to receive the proximal and distal deployable members. The proximal and distal deployable members are configured to be held in the contracted states when disposed within the hollow lumen. In the contracted states, the proximal and distal deployable members may be oriented in substantially longitudinally directions with respect to the insertion tool.

In use, the loop portion of the closure member may be positioned around at least one of the proximal deployable members of the first tacking device, and further positioned around at least one of the proximal deployable members of the second tacking device. The loop portion of the closure member may be positioned over at least one of the proximal deployable members of the first tacking device, and further positioned under at least one of the other proximal deployable members of the first tacking device. A cinching member coupled to the loop portion then may be actuated to secure the positioning of the loop portion, thereby maintaining the positioning of the first and second tacking devices and the associated compressive force upon the opening.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 7 is a side-sectional view taken along line A--A of FIG. 6.

FIG. 8 is a side-sectional view showing multiple tacking devices deployed in expanded configurations.

FIG. 9 is a schematic view illustrating multiple deployed tacking devices used to treat the ventral hernia of FIG. 4.

DETAILED DESCRIPTION OF THE PREFERRED EMBODIMENTS

In the present application, the term "proximal" refers to a direction that is generally towards a physician during a medical procedure, while the term "distal" refers to a direction that is generally towards a target site within a patient's anatomy during a medical procedure.

Figure 1:
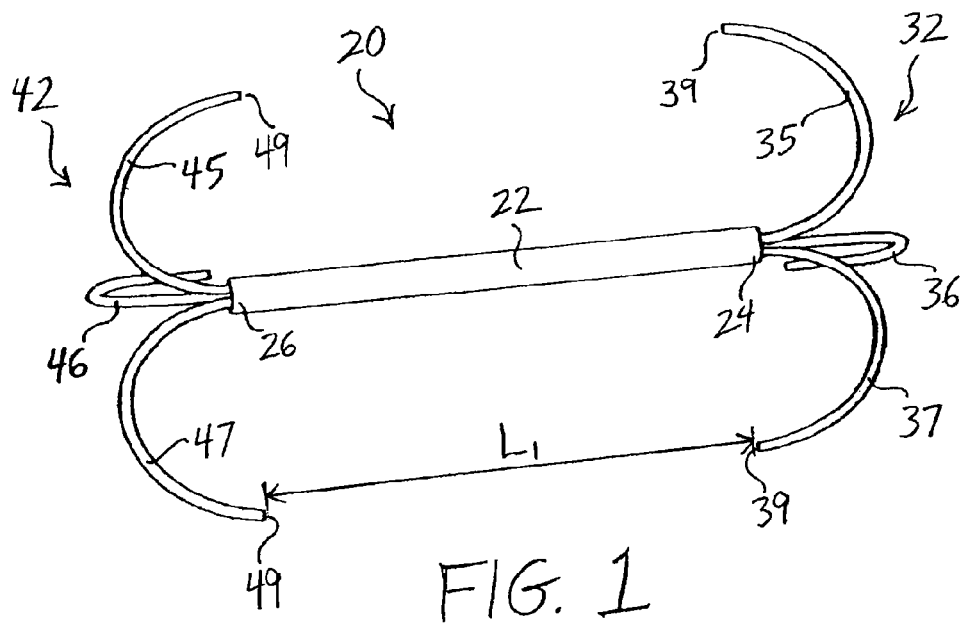
FIG. 1 is a perspective view of a tacking device.

Referring now to FIG. 1, a first embodiment of a tacking device 20 is shown. In this embodiment, the tacking device 20 comprises at least one tube member 22 having a proximal end 24 and a distal end 26. The tacking device 20 further comprises a proximal deployment mechanism 32 and a distal deployment mechanism 42. In the embodiment of FIG. 1, the proximal deployment mechanism 32 comprises three proximal deployable members 35-37, while the distal deployment mechanism 42 comprises three distal deployable members 45-47. The proximal deployable members 35-37 extend proximally from the proximal end 24 of the tube member 22, while the distal deployable members 45-47 extend distally from the distal end 26 of the tube member 22, as shown in FIG. 1. In the embodiment of FIG. 1, since the device is symmetrical, it may be loaded into an insertion tool with either end first, as explained further below.

The proximal deployable members 35-37 and the distal deployable members 45-47 each may be affixed relative to the tube member 22. In one embodiment, each of the proximal and distal deployable members 35-37 and 45-47 may be separate and discrete elements. Accordingly, six separate deployable members may be provided. Specifically, the three proximal deployable members 35-37 may be coupled to the tube member 22 near the proximal end 24 of the tube member 22. The three proximal deployable members 35-37 may be coupled to the proximal end 24 of the tube member 22 using an adhesive, frictional fit, mechanical device or other suitable mechanism or processes. Similarly, the three distal deployable members 45-47 may be coupled to the distal end 26 of the tube member 22 using an adhesive, frictional fit, mechanical device or other suitable mechanism.

In an alternative embodiment, instead of providing six discrete deployable members, three wires may be disposed through the entirety of tube member 22. In this embodiment, a first wire may comprise a proximal end that forms the deployable member 35 and a distal end that forms the deployable member 45, while a central region of the same wire is disposed through the entirety of the tube member 22. Similarly, second and third wires may be disposed through the entirety of the tube member 22 to form the remaining proximal and distal deployable members. In this embodiment, the three wires that extend through the length of the tube member 22 may be affixed to an interior surface of the tube member 22, for example, using an adhesive or mechanical device. The three wires also may be sized to create a frictional fit against each other and/or an interior surface of the tube member 22, thereby inhibiting movement of the proximal and distal deployable members 35-37 and 45-47 in longitudinal directions with respect to the tube member 22.

While six total deployable members 35-37 and 45-47 are depicted, including three at both the proximal and distal ends of the tacking device 20, it will be apparent that greater or fewer deployable members may be employed. Moreover, the deployable members 35-37 and 45-47 may comprise any shape suitable for engaging, penetrating and/or abutting tissue, for purposes explained further below, and need not necessarily assume the expanded shape depicted in FIGS. 1-2.

The tube member 22 may comprise any suitable shape and material. Solely by way of example, the tube member 22 may comprise stainless steel or a biocompatible plastic. The tube member 22 may be cylindrically-shaped, as depicted in FIG. 1, which may facilitate insertion through a lumen of an insertion tool 50. Further, the tube member 22 may comprise one solid tube, or alternatively may comprise one or more tubes that may comprise slots, holes, cut-out regions and the like, for example, as shown and explained below with respect to the embodiment of FIGS. 10-11.

Alternatively, as explained further below with respect to FIG. 10, the tube member 22 may be omitted entirely in the case where a first wire 125 integrally forms the proximal and distal deployable members 135 and 145, a second wire 126 integrally forms the proximal and distal deployable members 136 and 146, and a third wire 127 integrally forms the proximal and distal deployable members 137 and 147. In the latter embodiment, central regions of the first, second and third wires 125-127 may be affixed together, for example, using a solder or weld, to maintain the structural rigidity of the components.

Figure 2:
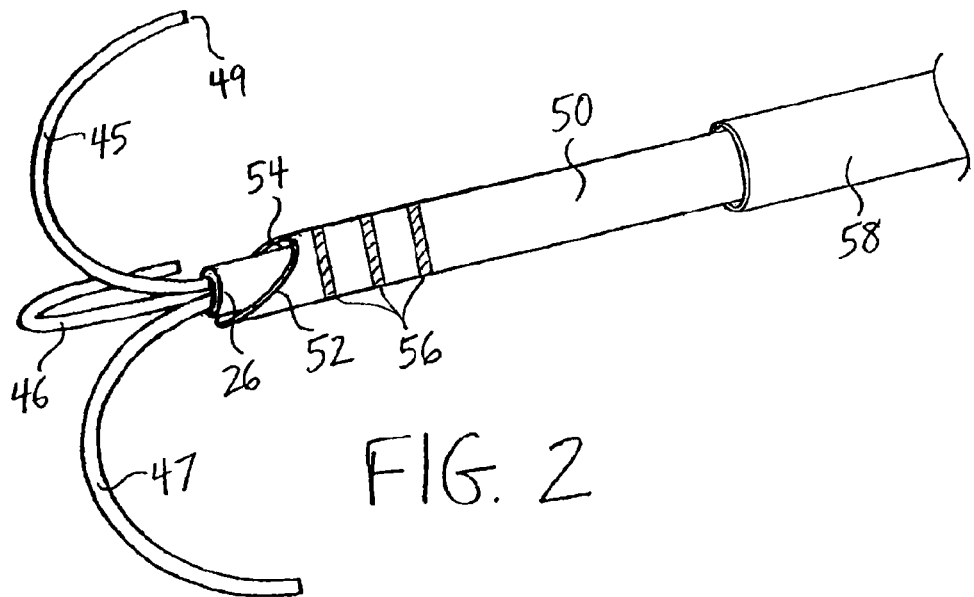
FIG. 2 is a perspective view of a distal region of an insertion tool and the tacking device of FIG. 1.
Figure 3:
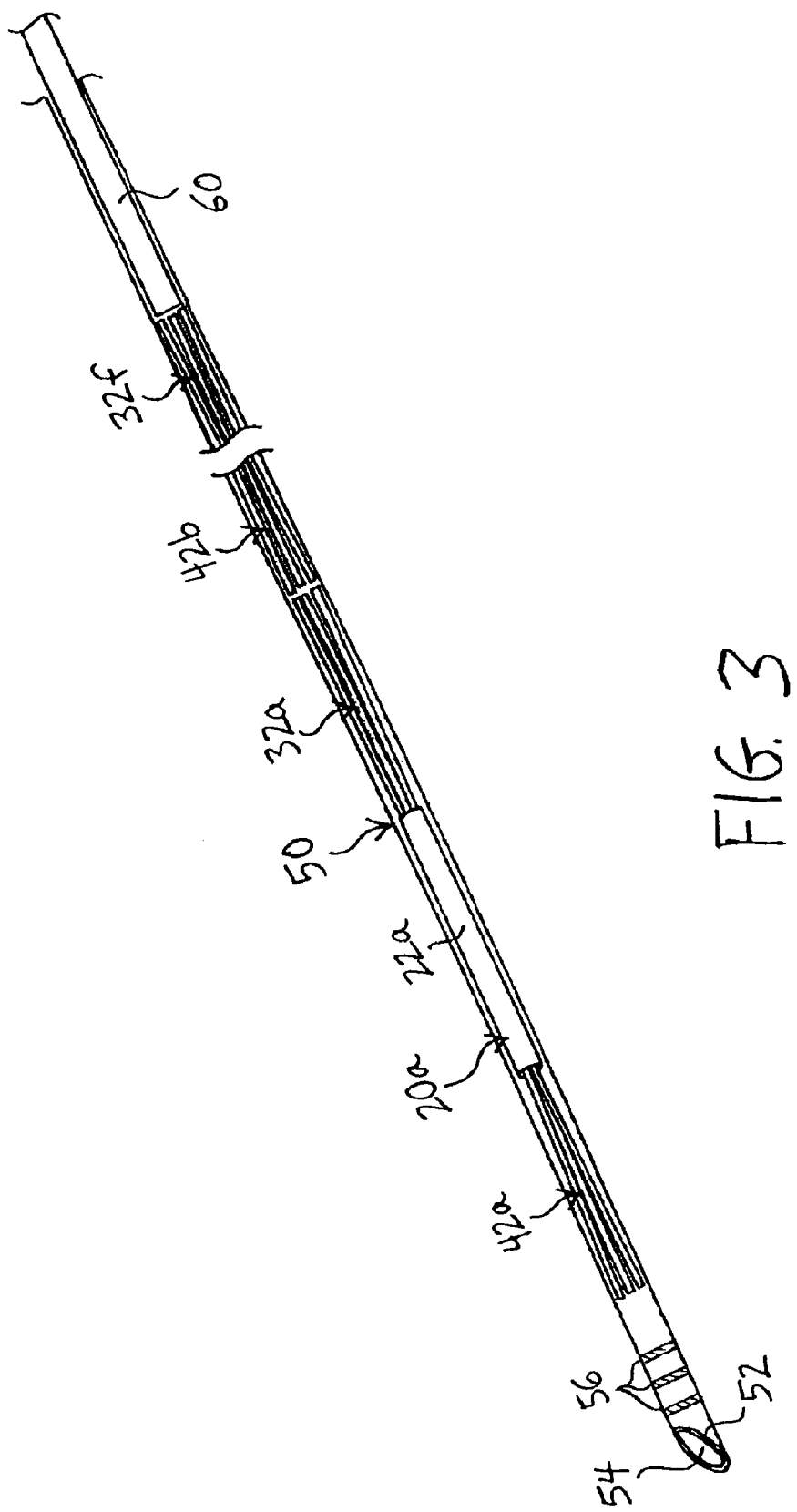
FIG. 3 is a perspective, cut-away view illustrating multiple tacking devices in a delivery configuration.

Referring still to FIGS. 1-3, the proximal and distal deployable members 35-37 and 45-47 each comprise a contracted delivery configuration, as shown in FIG. 3 below, and further comprise an expanded deployed configuration, as shown in FIG. 1. In one embodiment, each of the deployable members 35-37 and 45-47 may comprise a hook-shaped configuration in the expanded state. For example, the deployable members 35-37 and 45-47 may comprise a curvature of about 90 to about 360 degrees in the expanded state, and more preferably about 180 degrees, as shown in FIGS. 1-2. Where the deployable members 35-37 and 45-47 "retroflex" and comprises a curvature of about 180 degrees, the end regions 39 and 49 of the proximal and distal deployable members are oriented substantially parallel to the tube member 22. Moreover, the end regions 39 and 49 may be radially spaced apart from one another in the expanded state, as shown in FIG. 1. In this configuration, the end regions 39 and 49 may be well-suited for engaging, grasping, piercing and/or abutting tissue or graft material.

Further, a longitudinal distance $L_1$ between the end regions 39 and 49 of the tacking device 20 may be varied to engage tissue in a desirable manner. For example, the longitudinal distance $L_1$ may be dimensioned to be substantially equal to or less than the combined thickness $t_1$ and $t_2$ of a tissue 74 and a graft member 80, respectively, as shown in FIG. 8 below, thereby providing a desired compressive force upon the tissue 74 and the graft member 80.

The dimension of the tacking device 20 may be tailored based on a particular surgical procedure, a particular patient's anatomy and/or other factors. However, for illustrative purposes, in a ventral hernia repair operation, the longitudinal length of the tube member 22 may range from about 2 mm to about 10 mm, the straightened (delivery or non-curved) length of the proximal deployable members 35-37 may range from about 5 mm to about 50 mm, the straightened (delivery or non-curved) length of the distal deployable members 45-47 may range from about 5 mm to about 50 mm, the longitudinal distance $L_1$ between the end regions 39 and 49 may range from about 5 mm to about 30 mm, the outer diameter of the tube member 22 may range from about 0.3 mm to about 1.5 mm, and the outer diameter of the deployable member 35-37 and 45-47 may range from about 0.1 mm to about 0.5 mm. Such dimensions are provided for reference purposes only and are not intended to be limiting.

The deployable members 35-37 and 45-47 may comprise a shape-memory material, such as a nickel-titanium alloy (nitinol). If a shape-memory material such as nitinol is employed, the deployable members 35-37 and 45-47 may be manufactured such that they can assume the preconfigured expanded state shown in FIG. 1 upon application of a certain cold or hot medium. More specifically, a shape-memory material may undergo a substantially reversible phase transformation that allows it to "remember" and return to a previous shape or configuration. For example, in the case of nitinol, a transformation between an austenitic phase and a martensitic phase may occur by cooling and/or heating (shape memory effect) or by isothermally applying and/or removing stress (superelastic effect). Austenite is characteristically the stronger phase and martensite is the more easily deformable phase.

In an example of the shape-memory effect, a nickel-titanium alloy having an initial configuration in the austenitic phase may be cooled below a transformation temperature ($M_f$) to the martensitic phase and then deformed to a second configuration. Upon heating to another transformation temperature ($A_f$), the material may spontaneously return to its initial, predetermined configuration, as shown in FIG. 1. Generally, the memory effect is one-way, which means that the spontaneous change from one configuration to another occurs only upon heating. However, it is possible to obtain a two-way shape memory effect, in which a shape memory material spontaneously changes shape upon cooling as well as upon heating.

Alternatively, the deployable members 35-37 and 45-47 may be made from other metals and alloys that are biased, such that they may be restrained by the insertion tool 50 prior to deployment, but are inclined to return to their relaxed, expanded configuration upon deployment. Solely by way of example, the deployable members 35-37 and 45-47 may comprise other materials such as stainless steel, cobalt-chrome alloys, amorphous metals, tantalum, platinum, gold and titanium. The deployable members 35-37 and 45-47 also may be made from non-metallic materials, such as thermoplastics and other polymers. As noted above, the deployable members 35-37 and 45-47 may comprise any shape suitable for engaging, penetrating and/or abutting tissue, for purposes explained further below, and need not necessarily assume the curved shape depicted in FIGS. 1-2.

Referring to FIGS. 2-3, one or more tacking devices 20 may be delivered to a target site in a patient's anatomy using an insertion tool 50. In one embodiment, the insertion tool 50 is capable of carrying multiple different tacking devices, such as six tacking devices 20a-20f, as shown in FIG. 9 and described below. In FIG. 3, one complete tacking device 20a is shown in the contracted state, while portions of the proximal deployment mechanism 42b of another tacking device 20b, and the distal deployment mechanism 32f of another tacking device 20f, are also shown.

In one embodiment, the insertion tool 50 comprises a needle-like body having a sharpened distal tip 52 and a hollow lumen 54, as shown in FIGS. 2-3. The insertion tool 50 may be manufactured from stainless steel or any other suitable material, and may comprise an endoscopic ultrasound (EUS), or echogenic, needle. Solely by way of example, the insertion tool 50 may comprise the ECHOTIP® Ultrasound Needle, or the ECHOTIP® Ultra Endoscopic Ultrasound Needle, both manufactured by Cook Endoscopy of Winston-Salem, N.C.

The hollow lumen 54 of the insertion tool 50 may comprise an inner diameter that is larger than an outer diameter of the tacking device 20. Therefore, one or more tacking devices, such as six tacking devices 20a-20f, may be loaded into the hollow lumen 54 in a delivery configuration, as shown in FIG. 3. In the delivery configuration, the proximal and distal deployable members 35-37 and 45-47 of each tacking device 20a-20f may comprise a substantially longitudinally-oriented profile, i.e., oriented along a longitudinal axis of the insertion tool 50.

The multiple tacking devices 20a-20f may be inserted into the hollow lumen 54 of the insertion tool 50 in a sequential manner, whereby the proximal deployment mechanism 32a of the first tacking device 20a may abut the distal deployment mechanism 42b of the second tacking device 20b, as depicted in FIG. 3. The distal deployment mechanism 42a of the first tacking device 20a may be loaded a distance away from the sharpened distal tip 52 of the insertion tool 50 to prevent inadvertent deployment.

A stylet 60 may be disposed for longitudinal movement within the hollow lumen 52 of the insertion tool 50, as shown in FIG. 3. The stylet 60 may comprise stainless steel or any other suitable material. The stylet 60 is disposed proximal to the proximal deployment mechanism 32f of the final sequential tacking device 20f, as shown in FIG. 3. During use, the insertion tool 50 may be proximally retracted, while the stylet 60 may be held longitudinally steady, to facilitate sequential deployment of each of the tacking devices 20a-20f, as explained further below.

The insertion tool 50 may comprise one or more markers 56, as shown in FIGS. 2-3, which may be disposed near the distal end of the insertion tool 50. The markers 56 may be configured to be visualized under fluoroscopy of other imaging techniques to facilitate location of the distal end of the insertion tool, for example, so that a physician may determine how far the insertion tool 50 has penetrated into tissue 74, as depicted in FIGS. 7-8. Optionally, a sheath member 58 having an inner diameter larger than an outer diameter of the insertion tool 50, as shown in FIG. 2, may be longitudinally advanced over the insertion tool 50, for various purposes explained further below. As will be explained further below, the insertion tool 50 may be used in conjunction with another device, such as an endoscope, and may be delivered through a working lumen of an endoscope or similar device.

Referring now to FIGS. 4-9, one or more tacking devices 20 described above may be used to facilitate treatment of a perforation 75 using a graft member 80. In the example shown, the perforation 75 is a ventral hernia located in the abdominal wall 74. The right and left legs 72 and 73 of a patient 70 are shown for illustrative purposes. While treatment of a ventral hernia is shown for illustrative purposes, it will be apparent that the tacking devices described herein may be used in a wide range of medical procedures, including but not limited to any exemplary procedures described herein.

Figures 4, 5:
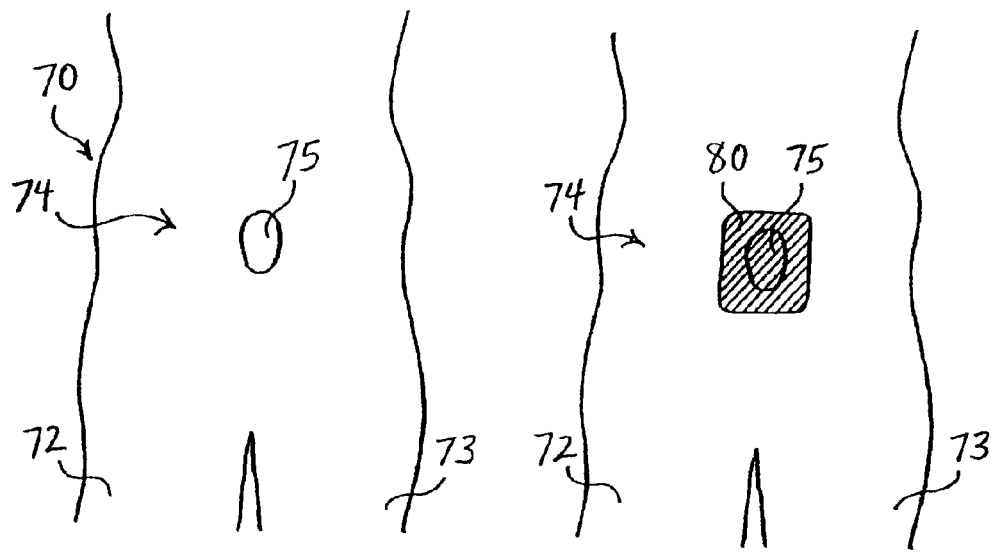
FIG. 4 is a schematic view illustrating a ventral hernia.
FIG. 5 is a schematic view illustrating a graft member used to cover the ventral hernia of FIG. 4.

The initial stages of the ventral hernia repair may be performed using techniques that are known. Specifically, an open technique or laparoscopic technique may be employed. In an open technique, an incision may be made in the abdominal wall and fat and scar tissue may be removed from the area. A graft member 80 then may be applied so that it overlaps the perforation 75, preferably by several millimeters or centimeters in each direction, as depicted in FIG. 5. In a laparoscopic technique, two or three smaller incisions may be made to access the hernia site. A laparoscope may be inserted into one incision, and surgical instruments may be inserted into the other incision(s) to remove tissue and place the graft member 80 in the same position as the open procedure.

The graft member 80 may comprise any suitable material for covering the perforation 75 and substantially or entirely inhibiting the protrusion of abdominal matter. In one embodiment, the graft member 80 may comprise small intestinal submucosa (SIS), such as SURGISIS® BIODESIGN™ Soft Tissue Graft, available from Cook Biotech, Inc., West Lafayette, Ind., which provides smart tissue remodeling through its three-dimensional extracellular matrix (ECM) that is colonized by host tissue cells and blood vessels, and provides a scaffold for connective and epithelial tissue growth and differentiation along with the ECM components. Preferably, the graft member 80 would be a one to four layer lyophilized soft tissue graft made from any number of tissue engineered products. Reconstituted or naturally-derived collagenous materials can be used, and such materials that are at least bioresorbable will provide an advantage, with materials that are bioremodelable and promote cellular invasion and ingrowth providing particular advantage. Suitable bioremodelable materials can be provided by collagenous ECMs possessing biotropic properties, including in certain forms angiogenic collagenous extracellular matrix materials. For example, suitable collagenous materials include ECMs such as submucosa, renal capsule membrane, dermal collagen, dura mater, pericardium, fascia lata, serosa, peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. The graft member 80 may also comprise a composite of a biomaterial and a biodegradeable polymer. Additional details may be found in U.S. Pat. No. 6,206,931 to Cook et al., the disclosure of which is incorporated herein by reference in its entirety.

Figure 6:
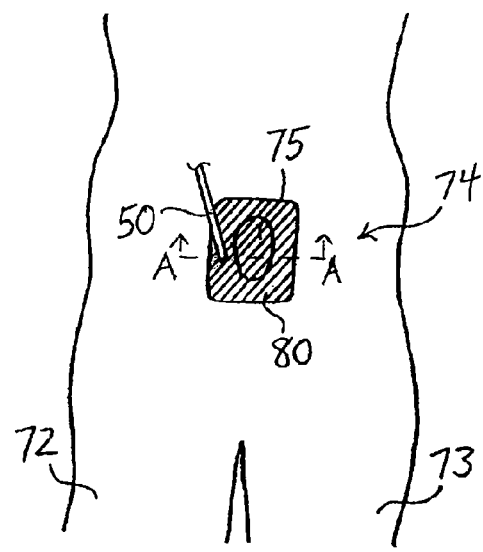
FIG. 6 is a schematic view of a method step for treating the ventral hernia of FIG. 4.

Referring now to FIGS. 6-7, after the graft member 80 has been placed to cover the perforation 75, the insertion tool 50 may be advanced in a distal direction to pierce through the graft member 80, and further may pierce at least partially into the tissue 74 at a first location around the perimeter of the perforation 75. In this example, the insertion tool 50 is carrying six sequential tacking devices 20a-20f, which may be disposed within the hollow lumen 54 of the insertion tool 50 as shown and explained with respect to FIG. 3 above. With each of the tacking devices 20a-20f in the contracted delivery states, the sharpened tip 52 of the insertion tool 50 may be advanced to a predetermined depth into the tissue 74. The markers 56 of FIGS. 2-3 may facilitate in determining how far the insertion tool 50 has penetrated into tissue 74, as depicted in FIG. 7.

In a next step, the stylet 60 of FIG. 3 may be held steady with respect to the insertion tool 50, while the insertion tool 50 is retracted in a proximal direction. This causes the distal deployable members 45-47 of the most distal tacking device 20a to extend distal to the sharpened tip 52 of the insertion tool 50, as depicted in FIG. 7. When the distal deployable members 45-47 are no longer radially constrained by the insertion tool 50, they may assume their predetermined expanded configurations in which they may engage, penetrate and/or abut the tissue 74. As the insertion tool 50 further is retracted proximally with respect to the tacking device 20a, the proximal deployable members 35-37 may assume their predetermined expanded configuration when are no longer radially constrained, as shown in FIG. 7. In the expanded configuration, the proximal deployable members 35-37 may engage, penetrate and/or abut the graft member 80 and optionally penetrate into the tissue 74. In this manner, the tacking device 20a helps secure the graft material 80 against the tissue 74. In particular, the substantially 180-degree hook-shaped configuration of the proximal deployable members 35-37 may urge the graft member 80 in a distal direction towards the tissue 74.

After the first tacking device 20a has been deployed, the insertion tool 50 may be repositioned to deploy another tacking device around the perimeter of the perforation 75. Each subsequent tacking device 20b-20f may be deployed in the same manner as the tacking device 20a. In this manner, the tacking devices 20a-20f may secure the graft member 80 around the perimeter of the perforation 75, as shown in FIG. 9. As will be apparent, greater or fewer tacking devices may be used, and the positioning of the tacking devices may be varied to optimize securing the graft member 80 to the tissue 74 in order to substantially seal the perforation 75.

Optionally, the sheath member 58 of FIG. 2 may be longitudinally advanced over the insertion tool 50, for example, if needed to protect the sharpened distal tip 52 of the insertion tool 50 while the insertion tool 50 is being repositioned. Further, the sheath member 58 may be advanced distally over the insertion tool 50 to facilitate deployment of the proximal deployable members 35-37. For example, the sheath member 58 may periodically push against the graft member 80, thereby temporarily urging the graft member 80 and/or the tissue 74 in a distal direction. At this time, the sheath member 58 may be held steady while the insertion tool 50 is retracted proximally to deploy the proximal deployable members 35-37 at a location proximal to the compressed tissue 74 and graft member 80. Once the proximal deployable members 35-37 have been deployed, the compressive force applied by the sheath member 58 may be removed so that the graft member 80 and the tissue 74 may engage the deployed proximal deployable members 35-37.

In the embodiment of FIGS. 4-9, the tissue 74 illustratively comprises a thickness $t_1$, while the graft member 80 comprises a thickness $t_2$. The distal deployable members 45-47 may be deployed entirely within the tissue 74, as depicted in FIG. 8, or alternatively may be deployed substantially distal to the tissue 74 while abutting or piercing through a distal edge of the tissue 74. In the latter embodiment, the longitudinal distance $L_1$ between the end regions 39 and 49 of the tacking device 20 may be dimensioned to be substantially equal to, or slightly less than, the combined thickness $t_1 + t_2$ of the tissue 74 and the graft member 80. The longitudinal distance $L_1$ may be otherwise sized and configured, as desired, to apply desired forces upon the graft member 80 and the tissue 74.

While FIGS. 4-9 have illustrated the use of one or more tacking device 20 for covering a perforation 75 formed in the ventral abdominal wall, the tacking devices disclosed herein may be useful in many other procedures. Solely by way of example, one or more tacking devices 20 may be used to treat perforations in a visceral wall, such as the stomach wall. In such cases, a suitable insertion device, such as an endoscope, may be advanced through a bodily lumen such as the alimentary canal to a position proximate the target location. One or more components may be advanced through a working lumen of the endoscope. To close the perforation, the graft member 80 may cover the perforation and may be secured in a position overlapping the perforation using the one or more of the tacking devices 20, which may be deployed using the techniques described hereinabove.

Figure 10:
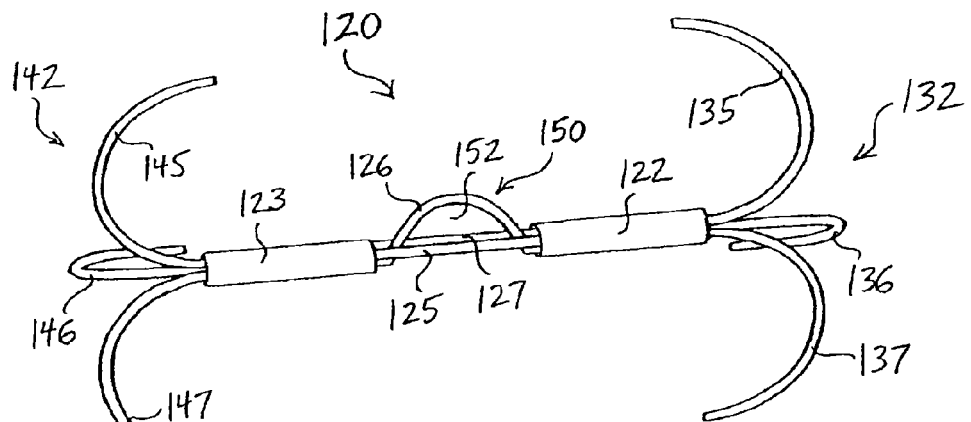
FIG. 10 is a perspective view of an alternative tacking device.

Referring now to FIG. 10, in an alternative embodiment, a tacking device 120 may comprise one or more features for facilitating suturing, and preferably purse-string suturing. The tacking device 120 is similar to the tacking device 20 of FIG. 1, except as noted below. The tacking device 120 comprises proximal and distal deployable members 135-137 and 145-147, respectively. In this embodiment, the tacking device 120 comprises a proximal tube portion 122 and distal tube portion 123 with an opening, slot or cutout disposed therebetween, as shown in FIG. 10. First, second and third wires 125-127 may be disposed through the entirety of the proximal and distal tube portions 122 and 123, as depicted in FIG. 10.

The first wire 125 may comprise a proximal end that forms deployable member 135 and a distal end that forms deployable member 145, such that a central region of the first wire 125 is disposed through both tube portions 122 and 123. Similarly, the second and third wires 126 and 127 may be disposed through the entirety of the tube portions 122 and 123. The second wire 126 may comprise a proximal end that forms deployable member 136 and a distal end that forms deployable member 146, while the third wire 127 may comprise a proximal end that forms deployable member 137 and a distal end that forms deployable member 147. The three wires 125-127 may be affixed to an interior surface of the tube portions 122 and 123, for example, using an adhesive, frictional fit or mechanical device. Alternatively, the tube portions 122 and 123 may be omitted, and central regions of the first, second and third wires 125-127 may be affixed to one another, for example, using a solder or weld.

In the embodiment shown, the second wire 126 comprises a loop member 150, which may be formed by bending a central region of the wire that is disposed between the tube portions 122 and 123, as shown in FIG. 10. The second wire 126 may be bent to form an arch-shaped loop member 150 having an aperture 152. A suture 160 may be threaded through the aperture 152 of the loop member 150, for example, as shown in FIG. 11 below.

In alternative embodiments, one single tube member may be employed, in lieu of the proximal and distal tube portions 122 and 123, and the single tube member may comprise a slot or cutout, such that the loop member 150 may extend radially through the slot or cutout. There also may be a single strip of material connecting the proximal and distal tube portions 122 and 123. Further, the loop member 150 need not be formed integrally from any of the wires 125-127, but rather may be formed as a loop disposed on an exterior surface of the proximal and distal tube portions 122 and 123, or on an exterior surface of a single tube member if only one tube is used. Still further, while the loop member 150 is shown in a substantially central location, it may be placed closer to the proximal or distal ends of the tacking device 120.

Figure 11:
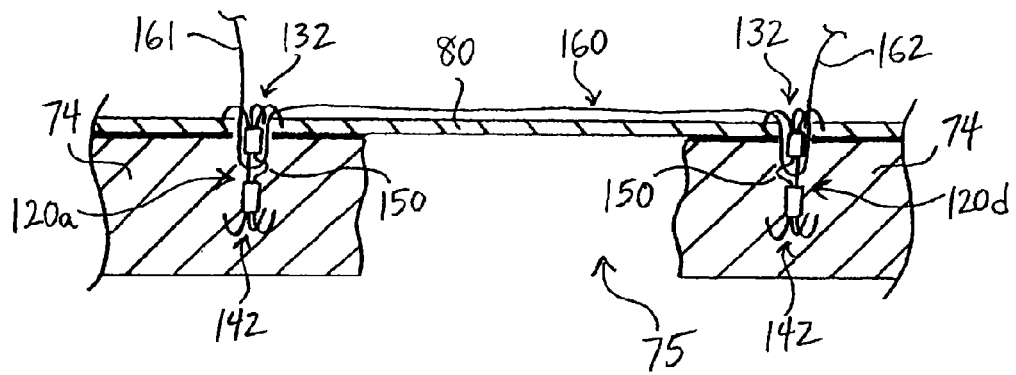
FIG. 11 is a side-sectional view illustrating one method of use of multiple tacking devices of FIG. 10.

Referring now to FIG. 11, an exemplary method of using the tacking device 120 is shown. In one step, a graft member 80 may be placed over a perforation 75, and multiple tacking devices 120 may be deployed using an insertion device to secure the graft member 80 to the tissue 74, as explained in detail above with respect to FIGS. 4-9. In the embodiment of FIG. 11, multiple tacking devices 120 may be linked together by a single suture 160, which may be slidably coupled through the loop members 150 of each of the tacking devices 120, as generally shown in FIG. 11. There are two free ends 161 and 162 of the suture 160, which may be independently tensioned to facilitate closure of the perforation 75.

Preferably, multiple tacking devices 120 having loop members 150 are sequentially positioned around the perforation 75 in a semi-annular or annular shape, for example, as shown above in FIG. 9. The ends 161 and 162 of the suture 160 are then tensioned to reduce the distance between the tacking devices and compress the tissue 74 around the perforation 75. The suture ends 161 and 162 may be secured to maintain the compression of the tissue 74 using any suitable technique such as by forming a knot or using clamps, rivets and the like.

Further, in lieu of the loop members 150 described herein, other mechanisms for engaging and/or retaining sutures may be integrally formed with the tacking device 120 or externally attached thereto. Solely by way of example, such suture retaining mechanisms are explained in pending U.S. patent application Ser. No. 11/946,565, filed Nov. 28, 2007, the entire disclosure of which is hereby incorporated by reference in its entirety.

Various types of sutures 160 may be used in conjunction with embodiment of FIGS. 10-11. For example, synthetic sutures may be made from polypropylene, nylon, polyamide, polyethylene, and polyesters such as polyethylene terephthalate. These materials may be used as monofilament suture strands, or as multifilament strands in a braided, twisted or other multifilament construction.

While the examples shown above have illustratively described a tacking device that may be useful for coupling a graft member to tissue to cover and seal a perforation, the tacking devices 20 and 120 also may be used in other procedures. For example, the tacking devices 20 and 120 may be used to secure a graft member to tissue for reconstructing local tissue, and the like. Further, the tacking devices 20 and 120 may be used in an anastomosis procedure. In order to create an anastomosis, for example, multiple tacking devices 20 or 120 may be deployed in a circular manner to couple a proximal vessel, duct or organ to a distal vessel, duct or organ. In such cases, a suitable insertion device, such as an endoscope, may be advanced through a bodily lumen such as the alimentary canal to a position proximate the target location. One or more components, such as the insertion tool 50, may be advanced through a working lumen of the endoscope. The distal end of the insertion tool 50 may be viewed under fluoroscopy, or via optical elements of the endoscope, or by some other visualization technique. Under suitable visualization, multiple tacking devices then may be delivered at one time, for example, using the insertion tool 50. Then, a hole may be punched through the middle of the deployed tacking devices to create a flow path between the proximal and distal vessels/ducts/organs. It will be apparent that still further applications of the tacking devices 20 and 120 are possible. Moreover, the insertion tool 50 may be used with or without an endoscope or similar device.

Referring now to FIGS. 12-15, another exemplary use of the tacking device 20 is described. In FIGS. 12-15, a plurality of tacking devices 20 are used for facilitating closure of an opening 175 in tissue 174. The tissue 174 comprises a mucosal layer 177 and a serosal layer 178. By way of example, the opening 175 may be formed during a translumenal procedure, whereby the tissue 174 may comprise tissue of the stomach, small or large intestines, or another bodily passage.

Figure 12:
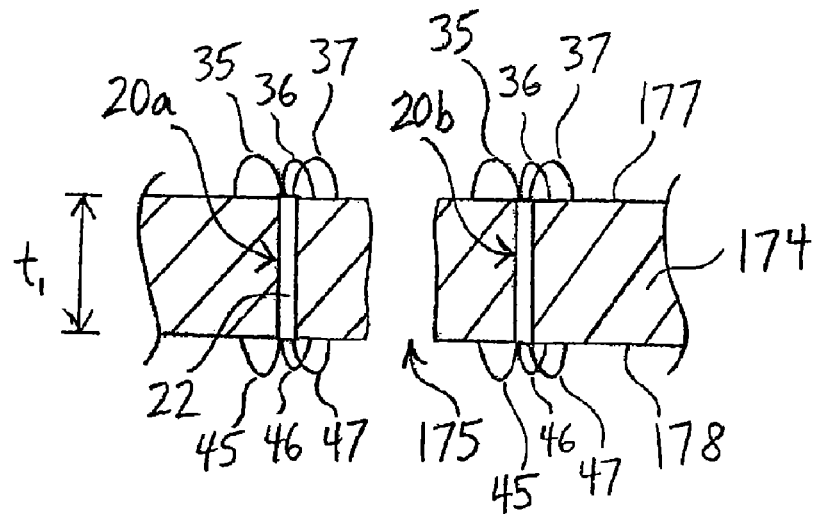
FIG. 12 is a side-sectional view showing multiple tacking devices deployed in the vicinity of an opening.
Figure 13:
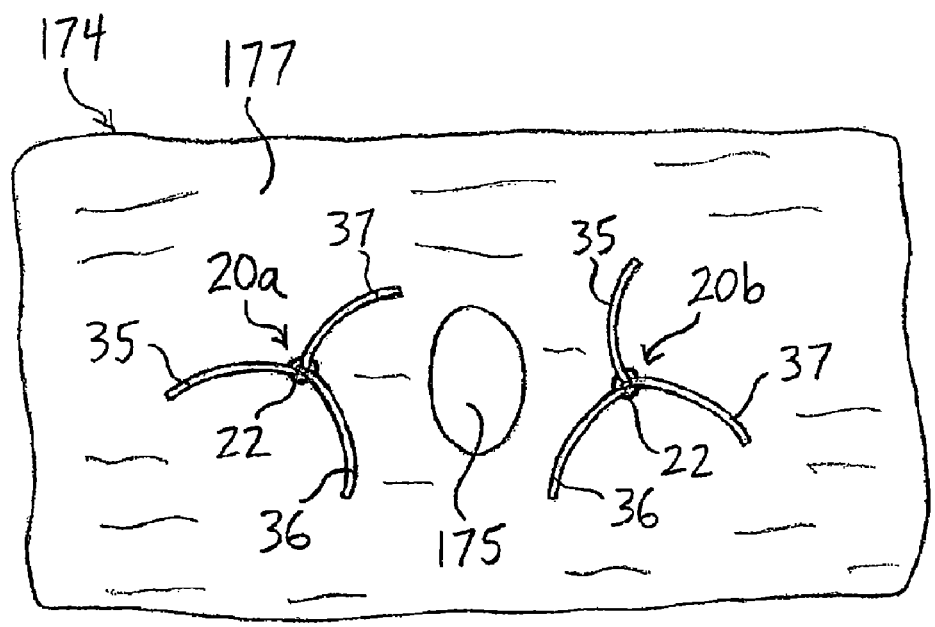
FIG. 13 is an upper perspective view of the tacking devices and the opening of FIG. 12.

In order to facilitate closure of the opening 175, a plurality of tacking devices 20 are disposed at least partially through the tissue 174 at one or more locations in the vicinity of the opening 175. Preferably, multiple tacking devices 20 at least partially surround the perimeter of the opening 175. In the embodiment of FIGS. 12-15, a first tacking device 20a is disposed on one side of the opening 175, and a second tacking device 20b is disposed on a substantially opposing side of the opening 175. The first and second tacking devices 20a and 20b may be delivered using an insertion tool 50, preferably in the manner described above. When deployed, the proximal deployable members 35-37 of each tacking device 20a and 20b may engage, abut or penetrate the mucosal layer 177 of the tissue 174. Further, the distal deployable members 45-47 of each tacking device 20a and 20b may engage, abut or penetrate the serosal layer 178 of the tissue 174, as best seen in FIG. 12. In this embodiment, the longitudinal distance $L_1$ between the end regions 39 and 49 of the tacking devices 20 (see FIG. 1) may be sized to be approximately equal to a thickness $t_1$ of the tissue 174.

Figure 14:
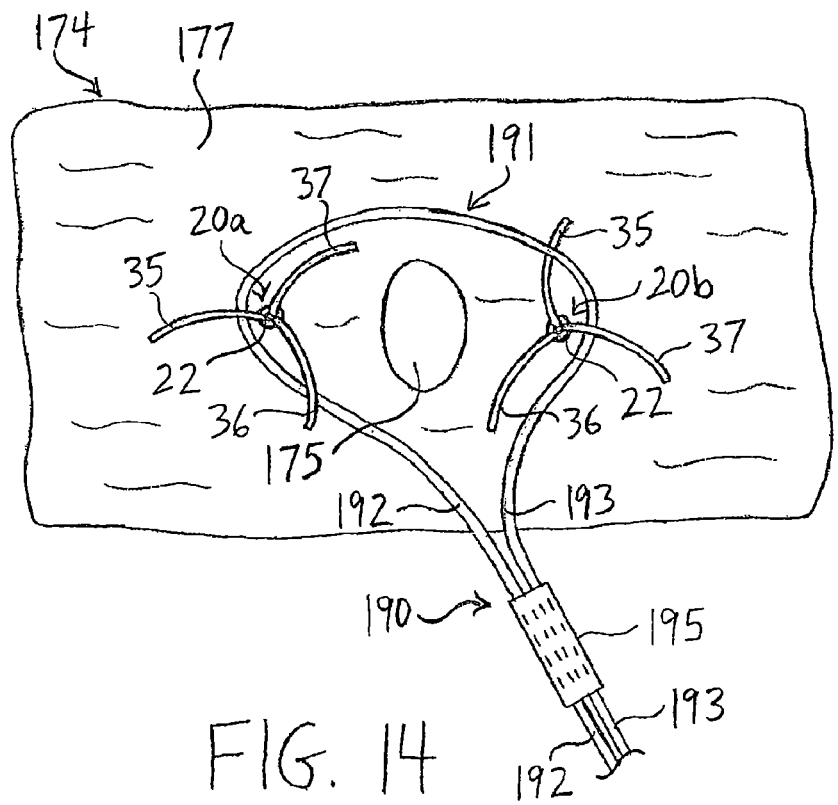
FIGS. 14-15 illustrate an exemplary method whereby multiple tacking devices are used to close the opening of FIGS. 12-13.
Figure 15:
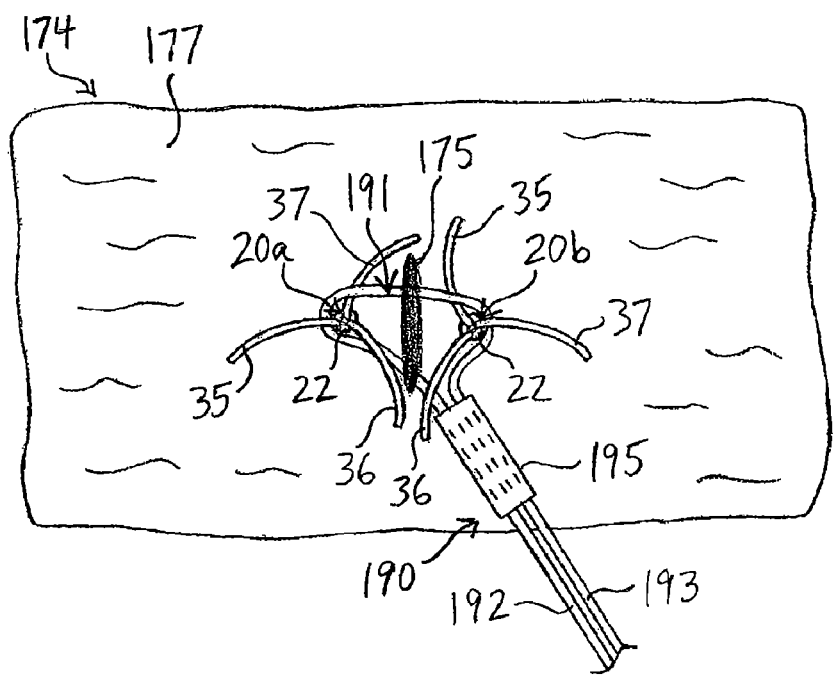

Referring to FIG. 14, a closure member 190 having a loop portion 191 may be positioned to surround at least a portion of the first and second tacking devices 20a and 20b. In one embodiment, the closure member 190 comprises first and second elongated portions 192 and 193, which may be formed from one or more elongated wires or sutures. The loop portion 191 may be formed between the first and second elongated portions 192 and 193, as shown in FIGS. 14-15.

The size and configuration of the loop portion 191 may be adjusted, e.g., using a cinching member 195. The cinching member 195 may be sized to surround the first and second elongated portions 192 and 193, as shown in FIGS. 14-15. In use, distal advancement of the cinching member 195 may decrease the size of the loop portion 191, as explained further below.

In order to facilitate closure of the opening 175, the loop portion 191 of the closure member 190 may be positioned to at least partially surround the first and second tacking devices 20a and 20b. For example, the loop portion 191 may be guided beneath at least one of the proximal deployable members 35-37 of each of the first and second tacking devices 20a and 20b. In this example, the proximal deployable members 35-37 of the first and second tacking devices 20a and 20b preferably are not substantially or permanently embedded into the mucosal layer 177, but rather may engage or abut the mucosal layer 177, to permit the loop portion 191 to slide between the proximal deployable members 35-37 and the tissue 174. If needed, a physician may increase the size of the loop portion 191 by proximally retracting the cinching member 195. With a desired loop configuration, the physician may maneuver the loop portion 191 as needed until it slides beneath at least one of the proximal deployable members 35-37 of each tacking device 20a and 20b, as depicted in FIG. 14. If the closure member 190 is delivered through a channel of an endoscope, the coupling of the loop portion 191 to the tacking devices 20a and 20b may be performed under endoscopic guidance, or with other direct or indirect visualization techniques, such as fluoroscopic or ultrasound imaging, e.g., using an endoscopic ultrasound endoscope.

The loop portion 191 may be used to push distally on the tissue 174 to create a gap between one of the deployable members 35-37 and the tissue 174 through which the loop portion 191 can be passed. This may further facilitate positioning of the loop portion 191, as shown in FIG. 14

Referring to FIG. 15, in a next step, a physician may distally advance the cinching member 195 to reduce the size of the loop portion 191. For example, a catheter or other pushing instrument may be advanced over the urge the cinching member 195 distally. This action may urge the first and second tacking devices 20a and 20b in inward directions, i.e., towards the opening 175, thereby applying a compressive force to facilitate closure of the opening 175, as shown in FIG. 15. It should be noted that the loop portion 191 may engage any of the proximal deployable members 35-37 and/or the tube member 22, if the tube member 22 is employed and extends above the mucosal layer 177.

Optionally, the cinching member 195 may comprise a locking feature, such that the positioning of the cinching member 195 may be secured to maintain the compressive force upon the opening 175. For example, a crimp may be imposed upon the cinching member 195 to secure its positioning relative to the first and second elongated portions 192 and 193. Alternatively, the cinching member 195 may click into place using a one-way ratcheting engagement with the first and second elongated portions 192 and 193. Still further, one or more external attachment devices, such as a clamp or ring, may be used to hold the cinching member 195 at a desired location.

As noted above, the loop portion 191 may be disposed around one or more of the proximal deployable members 35-37 of each tacking device 20a-20b. Preferably, the loop portion 191 is disposed beneath the hook-shaped portion of at least one of the proximal deployable members 35-37 of each tacking device 20a-20b to facilitate the provision of the inward compressive force noted above to close the opening 175. Further, it may be advantageous to place the loop portion 191 above the hook-shaped portion of at least one of the proximal deployable members 35-37 of each tacking device 20a-20b, as depicted in FIGS. 14-15. In particular, if the loop portion 191 is disposed partially above one or more proximal deployable members 35-37, then distal advancement of the cinching member 195 may cause the loop portion 191 to urge at least one of the proximal deployable members 35-37 towards the mucosal layer 177 to penetrate or further abut the tissue 174.

It should be noted that while two tacking devices 20a and 20b are shown in FIGS. 12-15 to facilitate closure of the opening 175, a greater number of tacking devices may be used, and the loop portion 191 may be disposed around portions of the additional tacking devices. Moreover, the tacking devices 20a and 20b may be deployed through the tissue 174 before or after creation of the opening 175. Finally, while a tube member 22 is depicted as part of the first and second tacking devices 20a and 20b in FIGS. 12-15, the tube member 22 may be omitted and the proximal and distal deployable members 35-37 and 45-47 may be integrally formed or otherwise adhered or coupled together without a tube member, as generally set forth above.

In further alternative embodiments, the apparatus and methods described herein may be used for facilitating closure of an opening in a layer of material, and are not restricted to methods for treatment of a human or animal body by surgery or therapy. For example, at least a portion of a first tacking device is disposed through at least a portion of the material at a first location in a vicinity of an opening in the layer of material. Then, at least a portion of a second tacking device is disposed through at least a portion of the material at a second location in the vicinity of the opening. A closure member having at least one loop portion is advanced towards the first and second tacking devices, and the loop portion is positioned around at least a portion of the first tacking device and at least a portion of the second tacking device. The closure member then is actuated to urge the first tacking device towards the second tacking device to provide a compressive force upon the opening, as generally described above.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A method for facilitating closure of a bodily opening, the method comprising:
   disposing at least a first portion of a first tacking device through at least a portion of tissue at a first location in a vicinity of an opening in the tissue, wherein the first tacking device comprises at least one proximal deployable member having contracted and expanded states;
   disposing at least a first portion of a second tacking device through at least a portion of the tissue at a second location in the vicinity of the opening in the tissue, wherein the second tacking device comprises at least one proximal deployable member having contracted and expanded states, wherein the first and second tacking devices are positioned such that the proximal deployable members are exposed on a proximal side of the tissue;
   advancing a closure member having at least one loop portion towards the first and second tacking devices;
   positioning the loop portion of the closure member around at least a second portion of the first tacking device and around at least a second portion of the second tacking device; and
   actuating the closure member to urge the first tacking device towards the second tacking device to provide a compressive force upon the opening,
   wherein the loop portion of the closure member is positioned around the at least one proximal deployable member of the first tacking device, and further positioned around the at least one proximal deployable member of the second tacking device,
   wherein the loop portion is advanced distally against the tissue to create a gap between at least one of the proximal deployable members and the tissue to facilitate positioning of the loop portion around the at least one of the proximal deployable members.

2. The method of claim 1 wherein the first and second tacking devices further each comprise at least one distal deployable member having contracted and expanded states.

3. The method of claim 2 further comprising:
   deploying the at least one distal deployable member of the first tacking device at a first location to engage a serosal layer of the tissue;
   deploying the at least one proximal deployable member of the first tacking device at a second location to engage a mucosal layer of the tissue;
   deploying the at least one distal deployable member of the second tacking device at a third location to engage the serosal layer of the tissue; and
   deploying the at least one proximal deployable member of the second tacking device at a fourth location to engage the mucosal layer of the tissue.

4. The method of claim 2 further comprising inserting the first and second tacking devices in a sequential manner within a hollow lumen of an insertion tool, wherein the first and second tacking devices are disposed within the hollow lumen with the proximal and distal deployable members in the contracted states.

5. The method of claim 1 further comprising:
   providing three proximal deployable members on the first tacking device for engaging the musocal layer of the tissue; and
   positioning the loop portion of the closure member over at least one of the proximal deployable members of the first tacking device, and further positioning the loop portion under at least one of the other proximal deployable members of the first tacking device.

6. The method of claim 1 further comprising actuating a cinching member to secure a configuration of the loop portion.

7. A method for facilitating closure of a bodily opening, the method comprising:
   disposing at least a portion of a first tacking device through at least a portion of tissue at a first location in a vicinity of an opening in the tissue;
   disposing at least a portion of a second tacking device through at least a portion of the tissue at a second location in the vicinity of the opening in the tissue, wherein the first and second tacking devices each comprise at least one proximal deployable member having contracted and expanded states, and further each tacking device comprising at least one distal deployable member having contracted and expanded states;
   delivering a closure member having a first elongate portion, a second elongate portion, and a loop portion disposed therebetween;
   positioning the loop portion of the closure member around at least a portion of the first tacking device and around at least a portion of the second tacking device;
   distally advancing a cinching member over the first and second elongate portions of the closure member to reduce the size of the loop portion, whereby reducing the size of the loop portion urges the first tacking device towards the second tacking device to provide a compressive force upon the opening;
   providing three proximal deployable members on the first tacking device for engaging a musocal layer of the tissue; and
   positioning the loop portion of the closure member over at least one of the proximal deployable members of the first tacking device, and further positioning the loop portion under at least one of the other proximal deployable members of the first tacking device.

8. The method of claim 7 wherein the closure member comprises an elongated wire.

9. The method of claim 7 wherein the closure member comprises an elongated suture.

10. The method of claim 7 further comprising:
    allowing at least one of the proximal deployable members of the first tacking device to self-expand to a hook-shaped configuration in the expanded state; and
    positioning the loop portion of the closure member beneath the hook-shaped configuration.

11. A method for facilitating closure of a bodily opening, the method comprising:
    providing a first tacking device comprising at least one proximal deployable member at least one distal deployable member, each having contracted and expanded states;
    providing a second tacking device comprising at least one proximal deployable member at least one distal deployable member, each having contracted and expanded states;
    inserting the first and second tacking devices in a sequential manner within a hollow lumen of an insertion tool, wherein the first and second tacking devices are disposed within the hollow lumen with the proximal and distal deployable members in the contracted states;
    advancing the insertion tool through a first portion of tissue in a vicinity of an opening;
    proximally retracting the insertion tool with respect to the first tacking device to cause the at least one distal deployable member of the first tacking device to expand and engage a serosal layer of the tissue and cause the at least one proximal deployable member of the first tacking device to expand and engage a mucosal layer of the tissue;

advancing the insertion tool through a second portion of the tissue in the vicinity of the opening;

proximally retracting the insertion tool with respect to the second tacking device to cause the at least one distal deployable member of the second tacking device to expand and engage the serosal layer of the tissue and cause the at least one proximal deployable member of the second tacking device to expand and engage the mucosal layer of the tissue;

positioning a closure member having a loop portion such that the loop portion is disposed around at least a portion of the first tacking device and around at least a portion of the second tacking device; and actuating the closure member to urge the first tacking device towards the second tacking device to provide a compressive force upon the opening, wherein the first tacking device comprises three proximal deployable members, and wherein the three proximal deployable members of the first tacking device are deployed to engage the mucosal layer of the tissue, the method further comprising positioning the loop portion of the closure member over at least one of the proximal deployable members of the first tacking device, and further positioning the loop portion under at least one of the other proximal deployable members of the first tacking device.

12. The method of claim 11 wherein in the step of positioning the closure member, the loop portion of the closure member is positioned around at least one of the proximal deployable members of the second tacking device.

13. The method of claim 11 wherein the first tacking device comprises at least one tube member having proximal and distal ends, wherein at least one proximal deployable member extends proximally from the proximal end of the tube member and the at least one distal deployable member extends distally from the distal end of the tube member, the method further comprising positioning the loop portion of the closure member around the tube member of the first tacking device.

14. The method of claim 11 further comprising providing a stylet disposed within the hollow lumen, wherein the stylet abuts the proximal deployable member of the second tacking device to facilitate retraction of the insertion tool with respect to the first and second tacking devices.

15. The method of claim 11 further comprising actuating a cinching member to secure a configuration of the loop portion.

16. A method for facilitating closure of a bodily opening, the method comprising:
disposing at least a first portion of a first tacking device through at least a portion of tissue at a first location in a vicinity of an opening in the tissue, wherein the first tacking device comprises at least one proximal deployable member having contracted and expanded states;

disposing at least a first portion of a second tacking device through at least a portion of the tissue at a second location in the vicinity of the opening in the tissue, wherein the second tacking device comprises at least one proximal deployable member having contracted and expanded states, wherein the first and second tacking devices are positioned such that the proximal deployable members are exposed on a proximal side of the tissue;

advancing a closure member having at least one loop portion towards the first and second tacking devices;

positioning the loop portion of the closure member around at least a second portion of the first tacking device and around at least a second portion of the second tacking device;

actuating the closure member to urge the first tacking device towards the second tacking device to provide a compressive force upon the opening;

providing three proximal deployable members on the first tacking device for engaging a musocal layer of the tissue; and positioning the loop portion of the closure member over at least one of the proximal deployable members of the first tacking device, and further positioning the loop portion under at least one of the other proximal deployable members of the first tacking device.

17. The method of claim 16 wherein the first and second tacking devices further each comprise at least one distal deployable member having contracted and expanded states.

18. The method of claim 17 further comprising:
deploying the at least one distal deployable member of the first tacking device at a first location to engage a serosal layer of the tissue;
deploying the proximal deployable members of the first tacking device at a second location to engage the mucosal layer of the tissue;
deploying the at least one distal deployable member of the second tacking device at a third location to engage the serosal layer of the tissue; and
deploying the at least one proximal deployable member of the second tacking device at a fourth location to engage the mucosal layer of the tissue.

19. The method of claim 17 further comprising inserting the first and second tacking devices in a sequential manner within a hollow lumen of an insertion tool, wherein the first and second tacking devices are disposed within the hollow lumen with the proximal and distal deployable members in the contracted states.

20. The method of claim 16 wherein in the step of positioning the loop portion of the closure member around at least a second portion, the loop portion of the closure member is further positioned around at least one of the proximal deployable members of the second tacking device.

21. The method of claim 20 wherein the loop portion is advanced distally against the tissue to create a gap between at least one of the proximal deployable members and the tissue to facilitate positioning of the loop portion around the at least one proximal deployable member.

22. The method of claim 16 further comprising actuating a cinching member to secure a configuration of the loop portion.

* * * * *

UNITED STATES PATENT AND TRADEMARK OFFICE
CERTIFICATE OF CORRECTION

PATENT NO. : 8,192,461 B2  Page 1 of 1
APPLICATION NO. : 12/557204
DATED : June 5, 2012
INVENTOR(S) : Michael L. Kochman et al.

It is certified that error appears in the above-identified patent and that said Letters Patent is hereby corrected as shown below:

In the Claims

In column 13, claim 1, line 35, after "loop portion around" delete "the".

In column 13, claim 5, line 61, after "engaging the" replace "musocal" with --mucosal--.

In column 14, claim 7, line 30, after "for engaging a" replace "musocal" with --mucosal--.

In column 16, claim 16, line 16, after "for engaging a" replace "musocal" with --mucosal--.

Signed and Sealed this
Second Day of October, 2012

David J. Kappos
*Director of the United States Patent and Trademark Office*